United States Patent
Parker et al.

(10) Patent No.: US 12,376,819 B2
(45) Date of Patent: Aug. 5, 2025

(54) IN-VIVO QUANTIFICATION OF FAT CONTENT IN AN ORGAN OF A LIVING SUBJECT USING ULTRASOUND

(71) Applicant: University of Rochester, Rochester, NY (US)

(72) Inventors: Kevin J. Parker, Rochester, NY (US); Juvenal Ormachea, Bellevue, WA (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 0 days.

(21) Appl. No.: 17/655,372

(22) Filed: Mar. 18, 2022

(65) Prior Publication Data

US 2022/0296207 A1    Sep. 22, 2022

Related U.S. Application Data

(60) Provisional application No. 63/164,107, filed on Mar. 22, 2021.

(51) Int. Cl.
*A61B 8/08*     (2006.01)
*A61B 8/00*     (2006.01)

(52) U.S. Cl.
CPC ............... *A61B 8/08* (2013.01); *A61B 8/485* (2013.01)

(58) Field of Classification Search
CPC .................................. A61B 8/08; A61B 8/485
See application file for complete search history.

(56) References Cited

U.S. PATENT DOCUMENTS

| | | | | |
|---|---|---|---|---|
| 2007/0134725 A1* | 6/2007 | Slawin | ................... | G16H 50/30 435/7.1 |
| 2019/0125308 A1* | 5/2019 | Rosenzweig | ........ | A61B 8/5207 |
| 2020/0205786 A1* | 7/2020 | Labyed | ................... | A61B 8/485 |
| 2020/0390421 A1* | 12/2020 | Audière | ................ | A61B 8/085 |
| 2020/0405265 A1* | 12/2020 | Labyed | ............... | G01S 7/52036 |

OTHER PUBLICATIONS

O., Quispe, "Viscoelastic Tissue Characterization Based on Harmonic and Transient ShearWave Elastography." Thesis Dissertation (Year: 2020).*
Apfel RE. Prediction of tissue composition from ultrasonic measurements and mixture rules. J Acoust Soc Am 1986;79:148-52.
Blackstock DT. Fundamentals of physical acoustics. New York: Wiley, pp. Ch. 9, 2000.
Carstensen EL, Parker KJ. Physical models of tissue in shear fields. Ultrasound Med Biol 2014;40:655-74.

(Continued)

*Primary Examiner* — Amal Aly Farag
(74) *Attorney, Agent, or Firm* — Ping Wang; Kalos Athena Wang PLLC

(57) ABSTRACT

A method is disclosed for determining the percent volume of fat in an organ (advantageously, the liver) of a living subject. Radiation (advantageously shear waves of known frequency and amplitude) is directed into the liver. The speed with which the radiation propagates within the liver, and the attenuation of the amplitude of the radiation caused by the liver, are measured. From these measured quantities, the percent volume of fat in the liver can be determined. The determination can be carried out by calculation, or by using a nomogram.

11 Claims, 2 Drawing Sheets

(56) References Cited

OTHER PUBLICATIONS

Christensen RM. Viscoelastic properties of heterogeneous media. J Mech Phys Solids 1969;17:23-41.

Cowin GJ, Jonsson JR, Bauer JD, Ash S, Ali A, Osland EJ, Purdie DM, Clouston AD, Powell EE, Galloway GJ. Magnetic resonance imaging and spectroscopy for monitoring liver steatosis. J Magn Reson Imaging 2008;28:937-45.

Ferraioli G. Non-invasive assessment of liver steatosis. Ultrasound Med Biol 2019;45:S32-S3.

Ferraioli G, Maiocchi L, Raciti MV, Tinelli C, De Silvestri A, Nichetti M, De Cata P, Rondanelli M, Chiovato L, Calliada F, Filice C. Detection of liver steatosis with a novel ultrasound-based technique: a pilot study using mri-derived proton density fat fraction as the gold standard. Clin Transl Gastroenterol 2019;10:e00081.

Jesper D, Klett D, Schellhaas B, Pfeifer L, Leppkes M, Waldner M, Neurath MF, Strobel D. Ultrasound-Based Attenuation Imaging for the Non-Invasive Quantification of Liver Fat—A Pilot Study on Feasibility and Inter-Observer Variability. IEEE J Transl Eng He 2020;8:1-9.

Kramer H, Pickhardt PJ, Kliewer MA, Hernando D, Chen GH, Zagzebski JA, Reeder SB. Accuracy of liver fat quantification with advanced CT, MRI, and ultrasound techniques: prospective comparison With MR spectroscopy. AJR Am J Roentgenol 2017;208. 92-100.

Lakes RS. Viscoelastic materials, Chapter 9. Cambridge ; New York: Cambridge University Press, pp. 2009.

Lee SS, Park SH. Radiologic evaluation of nonalcoholic fatty liver disease. World J Gastroenterol 2014;20:7392-402.

Lin Y-H, Wan Y-L, Tai D-I, Tseng J-H, Wang C-Y, Tsai Y-W, Lin Y-R, Chang T-Y, Tsui P-H. Considerations of ultrasound scanning approaches in non-alcoholic fatty liver disease assessment through acoustic structure quantification. Ultrasound Med Biol 2019;45:1955-69.

Mast TD. Empirical relationships between acoustic parameters in human soft tissues. Acoust Res Lett Onl 2000;1:37-42.

Nasr P, Fredrikson M, Ekstedt M, Kechagias S. The amount of liver fat predicts mortality and development of type 2 diabetes in non-alcoholic fatty liver disease. Liver Int 2020;40:1069-78.

Nguyen TN, Podkowa AS, Tam AY, Arnold EC, Miller RJ, Park TH, Do MN, Oelze ML. Characterizing fatty liver in vivo in rabbits, using quantitative ultrasound. Ultrasound Med Biol 2019;45:2049-62.

Ormachea J, Parker KJ. Comprehensive viscoelastic characterization of tissues and the inter-relationship of shear wave (group and phase) velocity, attenuation and dispersion. Ultrasound Med Biol 2020;46:3448-59.

Parker KJ. A microchannel flow model for soft tissue elasticity. Phys Med Biol 2014;59:4443-57.

Parker KJ. Experimental evaluations of the microchannel flow model. Phys Med Biol 2015;60:4227-42.

Parker KJ, Ormachea J, Drage MG, Kim H, Hah Z. The biomechanics of simple steatosis and steatohepatitis. Phys Med Biol 2018a;63:105013.

Parker KJ, Ormachea J, Will S, Hah Z. Analysis of transient shear wave in lossy media. Ultrasound Med Biol 2018b;44:1504-15.

Parker KJ, Partin A, Rubens DJ. What do we know about shear wave dispersion in normal and steatotic livers? Ultrasound Med Biol 2015;41:1481-7.

Parker KJ, Szabo T, Holm S. Towards a consensus on rheological models for elastography in soft tissues. Phys Med Biol 2019;64:215012.

Pirmoazen AM, Khurana A, El Kaffas A, Kamaya A. Quantitative ultrasound approaches for diagnosis and monitoring hepatic steatosis in nonalcoholic fatty liver disease. Theranostics 2020;10:4277-89.

Romero-Gómez M, Cortez-Pinto H. Detecting liver fat from viscoelasticity: How good is CAP in clinical practice? The need for universal cut-offs. J Hepatol 2017;66:886-7.

Sehgal CM, Brown GM, Bahn RC, Greenleaf JF. Measurement and use of acoustic nonlinearity and sound speed to estimate composition of excised livers. Ultrasound Med Biol 1986;12:865-74.

Sharma AK, Reis J, Oppenheimer DC, Rubens DJ, Ormachea J, Hah Z, Parker KJ. Attenuation of shear waves in normal and steatotic livers. Ultrasound Med Biol 2019;45:895-901.

Starekova J, Reeder SB. Liver fat quantification: where do we stand? Abdom Radiol (NY) 2020;45:3386-99.

Tamura K, Mamou J, Yoshida K, Hachiya H, Yamaguchi T. Ultrasound-based lipid content quantification using double-Nakagami distribution model in rat liver steatosis. Jpn J Appl Phys 2020;DOI: 10.35848/1347-4065/ab918e, in press.

Kia MF, Yan HM, He WY, Li XM, Li CL, Yao XZ, Li RK, Zeng MS, Gao X. Standardized ultrasound hepatic/renal ratio and hepatic attenuation rate to quantify liver fat content: an improvement method. Obesity (Silver Spring) 2012;20:444-52.

Younossi ZM, Koenig AB, Abdelatif D, Fazel Y, Henry L, Wymer M. Global epidemiology of nonalcoholic fatty liver disease—Meta-analytic assessment of prevalence, incidence, and outcomes. Hepatology 2016;64:73-84.

Zhang M, Castaneda B, Wu Z, Nigwekar P, Joseph JV, Rubens DJ, Parker KJ. Congruence of imaging estimators and mechanical measurements of viscoelastic properties of soft tissues. Ultrasound Med Biol 2007;33:1617-31.

Zhang YN, Fowler KJ, Hamilton G, Cui JY, Sy EZ, Balanay M, Hooker JC, Szeverenyi N, Sirlin CB. Liver fat imaging—a clinical overview of ultrasound, CT, and MR imaging. Br J Radiol 2018;91:20170959.

* cited by examiner

IN-VIVO QUANTIFICATION OF FAT CONTENT IN AN ORGAN OF A LIVING SUBJECT USING ULTRASOUND

SUMMARY OF THE INVENTION

The invention relates to diagnostic medical imaging, and more particularly relates to diagnostic medical imaging using ultrasound. In its most immediate sense, the invention relates to the use of ultrasound imaging to quantify the degree to which the liver (or other organ) of a living subject has been infiltrated by fat.

The noninvasive in vivo quantification of liver steatosis is a longstanding goal with major clinical significance. Although non-alcoholic fatty liver disease (NAFLD) is the most prevalent chronic liver disease, affecting approximately 25% of the global population, options for measuring and monitoring the progression of steatosis are limited.

Ultrasound imaging has been considered for the study of steatosis in livers, but currently has many limitations on accurate clinical quantification of fat. Many studies still use biopsies or MRI imaging to evaluate the degree to which a subject's liver has been infiltrated by fat. Liver biopsies are quite painful and MRI imaging is expensive, whereas ultrasound imaging has the advantages of being both noninvasive and inexpensive. It would therefore be advantageous to be able to quantify the fat content of the liver in vivo using ultrasound imaging.

Accordingly, one object of this invention is to provide a method of quantifying the fat content in the liver of a living patient using ultrasound, so as to avoid the need for surgical intervention such as a biopsy or for expensive imaging studies such as MRI.

The invention proceeds from the inventors' realization that an apparently unrelated model developed for use in materials science can be modified in such a manner as to accurately quantify fat content in the liver of a living subject when certain measured in vivo data are input to it. The original model, disclosed in Christensen R M, *Viscoelastic properties of heterogeneous media*. J Mech Phys Solids 1969; 17:23-41, provided a way to compute the elastic modulus of a composite material containing spherical inclusions. The inventors realized that a steatotic liver could fairly be treated as a composite material containing a low concentration of fat in the form of spherical inclusions.

But while being potentially useful, the existing model had the disadvantage that the number of unknown quantities exceeded the number of equations. In such circumstances, it was impossible to calculate all the unknowns, and it was consequently impossible to calculate the degree of steatosis. However, the inventors realized that the model could be simplified to have two equations and two unknown quantities and to therefore be capable of exact calculation. And, the two unknowns in the simplified model are quantities that can be measured in an ultrasound study, namely, 1) the speed of a shear waves within the liver and 2) the attenuation of shear waves induced by the liver. Hence, by measuring these two quantities, the fat content of the liver of a living subject could be calculated. These two quantities can easily be measured using an ultrasound imager that has an elastography feature.

Furthermore, the inventors realized that this conclusion justified the inference that calculation of steatosis could be carried out from other radiation, for example the speed and attenuation of ultrasound pulses, and not merely shear waves. Moreover, the inventors realized that their model would apply to any body structure organ in which a viscous material is embedded throughout an elastic matrix, and so could be used to calculate the percent volume of such viscous material by measuring the propagation speed of the ultrasound pulses within the organ and the amplitude attenuation of the pulses caused by the organ.

BRIEF DESCRIPTION OF THE DRAWINGS

The invention will be better understood with reference to the exemplary and non-limiting drawings, in which.

DETAILED DESCRIPTION OF PREFERRED EMBODIMENTS

Figure 1:
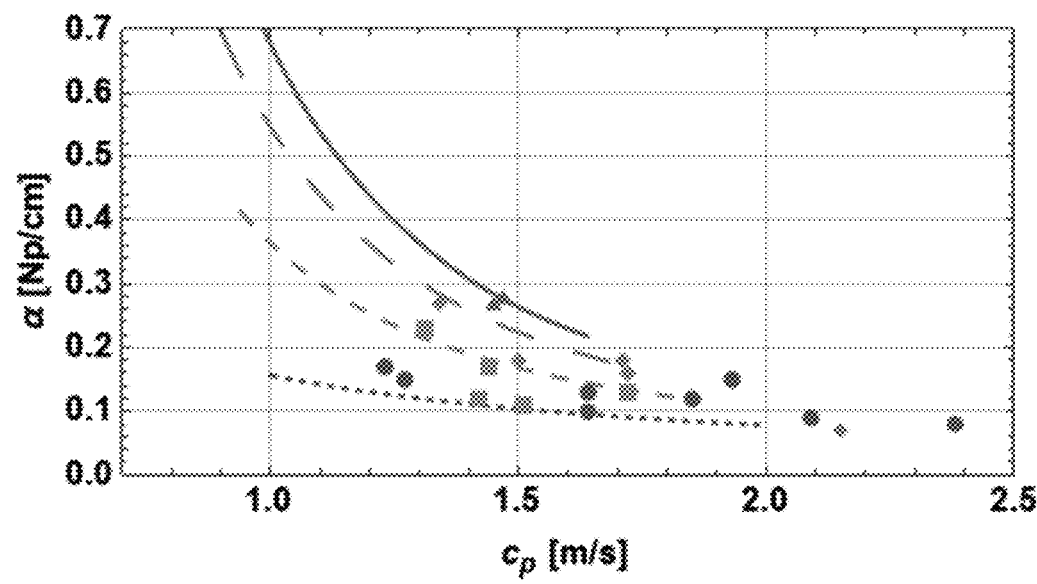
FIG. 1 compares the theory disclosed herein with experimental data. Viscosity=0.4 Pa-s for fat, showing patients with steatosis scores of S0 (circles), S1 (squares), S2 (diamonds), and S3 (triangles). Theoretical curves represent values of V equal to 0% (dotted line), 8% (small dash line), 15% (large dash line), and 20% (solid line) covering different liver shear modulus values, $G_1$, between 1 kPa and 4 kPa. The patient data are found to be stratified such that the two cases of S3 are located near the V=20% curve. The cases of S2 are located near the V=15% curve, with cases of lower grade steatosis below these.

A. Theoretical Basis for the First Preferred Embodiment

As stated above, we model a steatotic liver as a composite material; we treat it as a non-viscous matrix that contains a small fat fraction V of viscous fat that is distributed throughout the liver in the form of small spherical triglyceride-filled vesicles. The elastic modulus of such a material is disclosed in Christensen R M, *Viscoelastic properties of heterogeneous media*. J Mech Phys Solids 1969; 17:23-41. In the low concentration case for small volume fraction V of fat (triglyceride-filled spherical vacuoles) the shear modulus $G_2$ ($\omega$), in liver modeled as $G_1(\omega)$. Given $G_2$ ($\omega$), $G_1(\omega)$, and $V_2$, the new composite liver representing simple steatosis will have a shear modulus $G_c(\omega)$ given by:

$$\frac{G_c}{G_1} = 1 - \frac{15(1-v_1)\left(1-\frac{G_2}{G_1}\right)V_2}{7-5v_1+2(4-5v_1)\frac{G_2}{G_1}}. \tag{1}$$

Assuming the Poisson's ratio $v_1 \approx 0.5$, the incompressible limit, and writing the frequency dependence explicitly:

$$G_c(\omega) = G_1(\omega) - \frac{\frac{15}{2}[G_1(\omega) - G_2(\omega)]V_2}{\frac{9}{2} + 3\left[\frac{G_2(\omega)}{G_1(\omega)}\right]}. \quad (2)$$

Let us assume a generalized power law behavior for normal liver Thus, for normal liver and phantoms, we set $$G_1(\omega) = G_0(i\omega)^a = G_0 \cdot \omega^a \left[\cos\left(\frac{a\pi}{2}\right) + i\sin\left(\frac{a\pi}{2}\right)\right], \quad (3)$$

where $G_0$ is a constant, i is the imaginary number, and $\alpha$ is the power law parameter. Further assume a purely viscous fluid model for the fat within the spherical vacuoles:

$$G_2(\omega) = \eta \cdot i\omega, \quad (4)$$

where $\eta$ is the viscosity of the fat. In that case, the composite has a dramatic change in frequency response of $|G_c(\omega)|$, a function of the frequency and volume percent V, since the contribution from the fat has no real, elastic part and is purely imaginary. Once the $G_c(\omega)$ is specified, the storage modulus and loss modulus can be plotted from the real and imaginary parts of $G_c(\omega)$, respectively. In addition, the complex wavenumber $\hat{k}$ is specified as:

$$\hat{k} = \frac{\omega}{\sqrt{\frac{G_c(\omega)}{\rho}}} = \beta - j\alpha = \frac{\omega}{c_p} - j\alpha, \quad (5)$$

where $c_p$ is the phase velocity and $\alpha$ is the attenuation. These can be measured experimentally using clinical imaging platforms with appropriate elastography options Assuming $c_p$ and $\alpha$ have been measured accurately, we can determine $G_c(\omega)$ as:

$$G_c(\omega) = \frac{\rho\omega^2}{\left(\frac{\omega}{c_p} - i\alpha\right)^2} \quad (6)$$

To address the inverse problem, we now ask how V can be determined experimentally. Let us assume that the parameters in equation (4) are known for the fat vesicles; that both frequency and viscosity are known, and that $G_c(\omega)$ is also known from experimental measurements as in equation (6). Rewriting equation (2) we have:

$$G_c(\omega) = G_1(\omega) + \frac{5G_1[-G_1(\omega) + G_2(\omega)]V}{3G_1(\omega) + 2G_2(\omega)} \quad (7)$$

This is actually two equations, one for the real part and one for the imaginary part. To see this in a simpler fashion, we initially consider a special case where $G_2$ is purely imaginary (fat) and $G_1$ is purely real (elastic liver). In that special case, the real part of the composite $Re[G_c]$ and the imaginary part $Im[G_c]$ can be clearly separated:

$$Re[G_c] = G_1 + \frac{5G_1(-3G_1^2 + 2G_2^2)V}{9G_1^2 + 4G_2^2} \quad (8)$$

$$Im[G_c] = \frac{25G_1^2 G_2 V}{9G_1^2 + 4G_2^2}$$

And, Magnitude $[G_c] = \sqrt{Re^2 + Im^2}$. In this example, assuming $G_c$ is known accurately from measurements and equation (6), we then have two equations in two unknowns, namely $G_1$ (liver) and V (fat volume). The equations are cubic in $G_1$ and linear in V, and in principle these can be solved exactly, however any uncertainty in measurements or parameters will invalidate the system of equations, so numerical methods that are regularized are preferred.

Taking the real and imaginary parts of equation (6) numerically gives two values for equation (8) which can be solved numerically for $G_1$ and V. This value of V is an upper limit because equation (8) assumes all the loss is with the fat and the liver is purely elastic. Numerical solution routines are capable of finding the solution, or the global minimum of a corresponding minimization formulation. So the steps for quantifying liver fat volume percent are:

Measure $c_p$ and $\alpha$.
Find the real and imaginary parts of the right side of equation (6).
Substitute those into the equation (8) for $Re[G_c]$ and $Im[G_c]$ with $G_2 = \eta \times \omega$.
Solve numerically for $G_1$ and V.

B. Theoretical Basis for the Second Preferred Embodiment

As stated above, the first preferred embodiment of the invention assumes that $G_1$ (the liver shear modulus) is entirely real. To increase accuracy, a small imaginary term $G_{1,im}$ can be added to $G_1$ to approximate some baseline viscoelastic loss of normal liver. Thus, using Christensen's theory of composite media with inhomogeneous spherical inclusions, and assuming a nearly incompressible limit, we can rewrite equation (2) for the explicit case where the liver shear modulus (exclusive of any fat vacuoles) has a real part $G_1$ and an imaginary part $G_{1,im}$:

$$G_{comp}(\omega) = (G_1 + iG_{i,im}) + \frac{5(G_1 + iG_{1,im})[-(G_1 + iG_{1,im}) + iG_2]Vol}{3(G_1 + iG_{1,im}) + 2iG_2} \quad (9)$$

where $G_2$ represents the magnitude of the viscous fat term, equation (4). Now, separating out the real and imaginary parts of this we have:

$$Re[G_{comp}(\omega)] = G_1 - \frac{5G_1\left[3(G_1^2 + G_{1,im}^2) + 4G_{1,im}G_2 - 2G_2^2\right]Vol}{9G_1^2 + (3G_{1,im} + 2G_2)^2} \quad (10)$$

for the real, and then for the imaginary:

$$Im[G_{comp}(\omega)] = G_{1,im} + \frac{5\left[-3G_{1,im}(G_1^2 + G_{1,im}^2) + 5(G_1^2 + G_{1,im}^2)G_2 + 2G_{1,im}G_2^2\right]Vol}{9G_1^2 + (3G_{1,im} + 2G_2)^2} \quad (11)$$

As a check, in the limit as $G_{1,im}$ goes to zero, these equations revert back to the simpler form of equation (8).

The introduction of $G_{1,im}$ accounts for the lossy behavior of liver tissue that is expected in any viscoelastic material. However, it represents a third unknown unless set as an a priori value, from experimental results or rheological models. Based on our studies and others we have employed a simplification where $G_{1,im}$ is set at a small percent (around 5%) of $G_1$, thus reducing the unknowns in the equations to two: $G_1$ and V.

C. Third Preferred Embodiment (Nomogram)

Because numerical solutions require computer programs and can be sensitive to issues such as local minima, it is advantageous to have available a simple graphical solution, or nomogram, for clinical use. In this strategy the forward problem is calculated from equations (4)-(7) and the resulting theoretical values of a and c are plotted on a two-dimensional graph as a function of $\{V, G_1\}$ contours. In practical use, any pair of $\{\alpha, c\}$ measured from a patient is then located at a point on the graph which provides an immediate graphical estimate of the corresponding $\{V, G_1\}$ that are likely given the measured quantities. As an example, see FIG. 1. Note that as $c_p$ becomes larger than 1.5 the contours of constant V begin to converge, meaning small errors in $\alpha$ estimates will result in large errors in determining V. Also, there are combinations of $\{\alpha, c_p\}$ that are not possible within the assumptions of the model. In such instances, patient data falling outside of the ranges indicated would need to be re-examined, or the model revised.

D. Alternate Embodiment (Using Ultrasound and an Alternate Measure of Interaction With the Liver)

Other measures can fit within our framework, for example estimates of dispersion in a viscoelastic medium are linked by physics to the attenuation losses within that medium, and have been used to measure tissue characteristics. Dispersion measures related to attenuation can be employed, so long as an estimate of both real and imaginary parts of the shear modulus can be obtained and entered into the model.

Our framework can be extended to a calculation of V based on ultrasound speed of sound and ultrasound attenuation as well. In our framework, one proceeds by measuring the ultrasound speed of sound and attenuation of the tissue, then applying equations (5 and 6) where G is replaced by compressibility K for compression waves. Then, the real and imaginary parts of wavenumber are compared with the mixture or composite model, producing two equations in two unknowns (K of the liver and V of the fat volume percent) which can be solved numerically or by nomogram. However, the change in normal liver's speed of sound, with increasing amounts of steatosis, is a small percent compared to baseline. Thus, high precision in the measurements will be required, along with careful disentangling of any cofactors that also influence speed of sound and attenuation of the liver.

E. Validation of Results From Using the Invention

The results in phantoms and human livers show reasonable correlation of our quantitative solutions against independent measures of fat, however limitations of this method include the uncertainties in measurements of $\alpha$ and c, within clinical systems. Furthermore, the most accurate values of human fat viscosity, and the ratio of imaginary part of the liver shear modulus under different fibrotic states are not precisely known at this time. These can be refined by careful studies that measure both the shear wave properties and the chemical composition of livers under different states. For example, extraction and quantification of triglyceride properties from the vacuoles will provide improved estimates of the inherent viscosity term to be used in equation (4). Similarly the loss component of normal livers, exclusive of any fat, can be estimated from previous studies, however as a liver becomes fibrotic the loss tangent (exclusive of fat accumulation) may change, altering the relationship or proportionality of $G_1$ to $G_{1,im}$ in equations (9)-(11). These refined estimates should improve the performance of the model under a wider range of pathological conditions.

1. Validation Procedure

Livers and phantoms were scanned according to the protocols given in Sharma A K, Reis J, Oppenheimer D C, Rubens D J, Ormachea J, Hah Z, Parker K J. Attenuation of shear waves in normal and steatotic livers. Ultrasound Med Biol 2019; 45:895-901 and Parker K J, Ormachea J, Will S, Hah Z. Analysis of transient shear wave in lossy media. Ultrasound Med Biol 2018b; 44:1504-15. The numerical solution was implemented using a minimization procedure in Mathematica (Wolfram Research, Champaign, IL, USA) with simulated annealing to avoid entrapment in local minima. The minimization approach simply subtracts the real terms (right hand side) of equation (8) from the measured real modulus, which should approach zero as the correct values of V and $G_1$ are determined. This term is equally weighted with a similar subtraction of the imaginary part of equation (8). The search parameter space is also limited within realistic ranges, for example V<45% fat. Simulated annealing is utilized to avoid local minima. The specific routine is written as:

$$NMinimize\left[\left\{1 * \right.\right.$$
$$Abs\left[Gmeasured - \left(G1 - \frac{5\,G1\big(3(G1^2 + G1im^2) + 4G1imG2 - 2G2^2\big)Vol}{9G1^2 + (3\,G1im + 2G2)^2}\right)\right] +$$
$$Abs\left[GmeasIm - \left(G1im + \right.\right.$$
$$\left.\left.\frac{5\big(-3G1im(G1^2 + G1im^2) + (5G1^2 + G1im^2)G2 + 2G1imG2^2\big)Vol}{9G1^2 + (3G1im + 2G2)^2}\right)\right],$$
$$Vol \geq 0.001\ \&\&\ Vol < 0.45\ \&\&\ G1 > 700\ \&\&\ G1 < 12000\ \&\&$$
$$Gmeasured > 0.9\,Gexpt\ \&\&\ Gmeasured < 1.1\,Gexpt\ \&\&$$
$$\left.GmeasIm > 0.95GexpIm\ \&\&\ GmeasIm < 1.05GexpIm\right\},$$
$$\{Vol, G1, Gmeasured, GmeasIm\},$$
$$\left.Method \to \text{``SimulatedAnnealing''}\right]$$

where the unknowns are $G_1$ (the real part of the shear modulus of the liver) and Vol is the percent volume of fat vesicles. The simulated annealing search algorithm searches under constraints on the permitted values of V and $G_1$: $0.001 < V < 0.45$ and $700 < G_1 < 12{,}000$ Pa. Also, because of the imprecision of measurements, the search is permitted over a few percent variations in parameters derived from c and a in equation (6).

In addition, the Spearman's rank correlation coefficient and the analysis of variance (ANOVA) were used as a non-parametric measure of rank correlation, and to determine if the V results from the different patient group have a common mean, respectively. Both statistical tests were implemented on MATLAB (The MathWorks, Inc., Natick, MA, USA).

2. Validation Results

The derived values, from the composite material model, of the real and imaginary parts of the shear modulus for the oil-in-gelatin phantoms are given in Table 1. Note the general trend with increasing amounts of oil in the form of spherical inclusions is to lower (soften) the real modulus, and also to decrease the imaginary modulus, however this effect is strongly dependent on frequency.

TABLE 1

Shear moduli of oil-in-gelatin phantoms.

| Oil percent | Complex shear modulus G |
|---|---|
| 2% → | 4539.02 + 182.18i |
| 6% → | 4226.06 + 177.55i |
| 12% → | 3756.63 + 170.62i |
| 18% → | 3287.19 + 163.69i |
| 24% → | 2817.75 + 156.75i |
| 30% → | 2348.31 + 149.81i |
| 36% → | 1878.88 + 142.88i |

Figure 2:
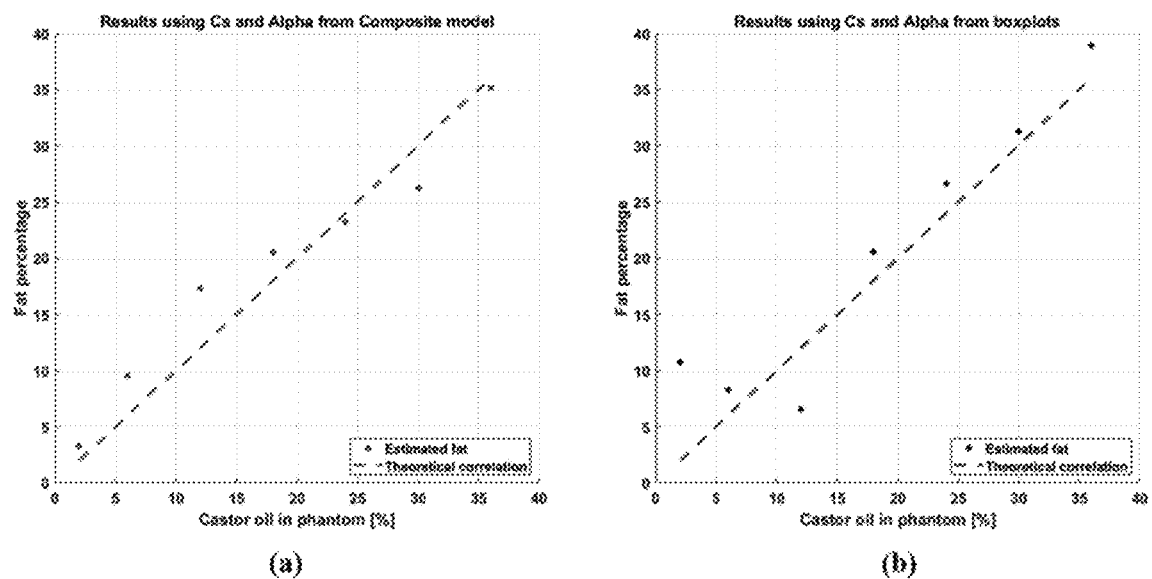
FIG. 2 shows the numerical solution of percent volume fat in the gelatin-based phantoms containing different amount of castor oil percentages as measured in Parker et al. (2018a). (a) V estimates as a function of increasing fat using the complex shear modulus values from Table 1 and (b) V estimates as a function of increasing fat using the median complex shear modulus when using the median results of shear wave speed and shear attenuation from FIGS. 9 and 10 of Parker et al. (2018a). The dashed lines represent a perfect correlation between the applied oil volume percentage in the phantoms and the V estimates.

FIG. 2 shows the numerical results for the numerical solution of percent volume fat in the phantoms. The numerical minimization search procedure was run on the oil-in-gelatin phantom series of experiments. FIG. 2(a) shows the numerical results using the complex shear modulus values from Table 1, and FIG. 2(b) shows the numerical results using the median complex shear modulus when using the median results of shear wave speed and shear attenuation from FIGS. 9 and 10 of Parker K J, Ormachea J, Drage M G, Kim H, Hah Z. The biomechanics of simple steatosis and steatohepatitis. Phys Med Biol 2018a; 63:105013.

Figure 3:
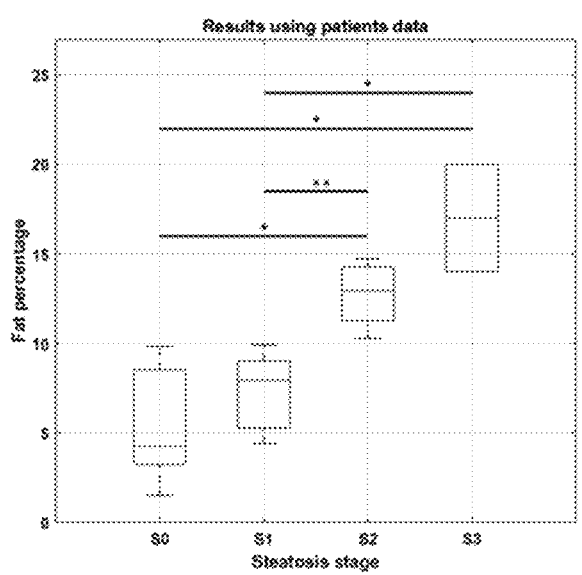
FIG. 3 shows the numerical solution of percent volume fat in 20 patients scanned in Sharma et al (2019). The steady increase in estimated V is observed and confirmed by a Spearman's rank correlation coefficient equal to 0.83. The ANOVA test shows that there is a significant difference between groups S0 and S2, S0 and S3, S1 and S2, and S1 and S3. *p>0.01, **p>0.05.

FIG. 3 shows the numerical estimates from 20 patients within the Sharma, et al. (2019) study, showing the estimated volume percent V of fat as a function of biopsy results scored for steatosis stages S0 to S3. The middle of the elastography region of interest (ROI) was placed between 3 and 6 cm deep and at least 1 to 2 cm below the capsule. Ten repeat elastography scans' ROIs were obtained near or in the sample plane as the biopsy. The steady increase in estimated V is observed. Then Spearman's rank correlation coefficient was 0.83 with p-value equals to 6.6350e-06. In addition, the ANOVA test shows that there is a significant difference between groups S0 and S2 (p=0.0013), and S3 (p=3.5965e-04). The same is true for groups S1 and S2 (p=0.0307), and S3 (p=0.0033). However, there is not a significant difference between groups S0 and S1 (p=0.6320), and between S2, and S3 (p=0.2843).

Although preferred embodiments of the invention have been described above, the scope of the invention is limited only by the following claims:

The invention claimed is:

1. A method for estimating a percent volume of fat within a liver of a living subject, comprising the following steps:
   a. physically generating ultrasound shear waves of known frequency and amplitude in the liver using diagnostic ultrasound imaging technology, wherein the ultrasound shear waves propagate therein;
   b. physically measuring a speed with which the ultrasound shear waves propagate within the liver;
   c. physically measuring an attenuation of the amplitude of the ultrasound shear waves caused by the liver;
   d. estimating, using computer software, a real part and an imaginary parts of the tissue modulus from the measured speed and interaction in the liver by applying (Eqns. 5 and 6):

$$\hat{k} = \frac{\omega}{\sqrt{\frac{G_c(\omega)}{\rho}}} = \beta - j\alpha = \frac{\omega}{c_p} - j\alpha, \quad (5)$$

$$G_c(\omega) = \frac{\rho\omega^2}{\left(\frac{\omega}{c_p} - i\alpha\right)^2}; \quad (6)$$

e. comparing, using computer software, the real and imaginary parts of the tissue modulus to a viscoelastic composite model of the liver to estimate the percent volume of viscous material within the liver, wherein the viscoelastic composite model considers the liver to be a composite material in which a fat fraction is distributed within the liver; and
   f. quantifying, the percent volume of viscous material within the liver from the viscoelastic composite model and the real and imaginary parts of the tissue modulus.

2. The method of claim 1, wherein the subject is a human being.

3. The method of claim 1 wherein the using step is carried out using a nomogram.

4. The method of claim 1, wherein steps 1 a, 1 b, and 1 c are carried out using an ultrasound scanner with an elastography feature.

5. A method for estimating a percent volume of the viscous material within a body structure of a living subject in which a viscous material is embedded throughout an elastic matrix, comprising the following steps:
   a. physically generating ultrasound radiation of known frequency and amplitude in the body structure using diagnostic ultrasound imaging technology, wherein the ultrasound radiation propagates therein;
   b. physically measuring a radiation speed with which the ultrasound radiation propagates within the body structure;
   c. physically measuring an interaction between the ultrasound radiation and the body structure;
   d. estimating using computer software, a real part and an imaginary parts of the tissue modulus from the measured ultrasound radiation speed and interaction in the body structure by applying (Eqns. 5 and 6):

$$\hat{k} = \frac{\omega}{\sqrt{\frac{G_c(\omega)}{\rho}}} = \beta - j\alpha = \frac{\omega}{c_p} - j\alpha, \quad (5)$$

$$G_c(\omega) = \frac{\rho\omega^2}{\left(\frac{\omega}{c_p} - i\alpha\right)^2}; \quad (6)$$

e. comparing, using computer software, the real and imaginary parts of the tissue modulus to a viscoelastic composite model of the body structure to estimate the percent volume of viscous material within the body structure; and f. quantifying, the percent volume of viscous material within the liver from the viscoelastic composite model and the real and imaginary parts of the tissue modulus, wherein the viscoelastic composite model considers the body structure to be a composite material in which a fat fraction is distributed within the body structure.

6. The method of claim 5, wherein the interaction is attenuation of the amplitude of the radiation caused by the body structure.

7. The method of claim 5, wherein the interaction is dispersion of the radiation within the body structure.

8. The method of claim 5, wherein the body structure is an organ of the subject.

9. The method of claim 5, wherein the body structure is a muscle of the subject.

10. The method of claim 5, wherein the radiation is ultrasound pulses.

11. The method of claim 5, wherein the radiation is shear waves.

* * * * *